United States Patent
Lin et al.

(10) Patent No.: US 6,870,237 B1
(45) Date of Patent: Mar. 22, 2005

(54) REPEATED STRUCTURE OF NANOMETER THIN FILMS WITH SYMMETRIC OR ASYMMETRIC CONFIGURATION FOR SPR SIGNAL MODULATION

(75) Inventors: Chii-Wann Lin, Taipei (TW); Chen Kung Huang, Taipei (TW); Shiming Lin, Taipei (TW); Chih Kung Lee, Taipei (TW); Peizen Chang, Taipei (TW); Shu Sheng Lee, Taipei (TW)

(73) Assignee: National Taiwan University, Taipei (TW)

( * ) Notice: Subject to any disclaimer, the term of this patent is extended or adjusted under 35 U.S.C. 154(b) by 6 days.

(21) Appl. No.: 10/647,229

(22) Filed: Aug. 26, 2003

(51) Int. Cl.⁷ ............................................... H01L 31/00
(52) U.S. Cl. ...................... 257/428; 257/414; 257/431; 977/DIG. 1
(58) Field of Search ................................ 257/414, 428, 257/431

Primary Examiner—Long Pham
(74) Attorney, Agent, or Firm—Rabin & Berdo, P.C.

(57) ABSTRACT

A symmetric or asymmetric multilayer structure based on the technique of surface plasmon resonance (SPR) has been applied for modulation of resonant angle and wavelength. The fabrication of this invention can have nanoscale thin film layers up to several hundreds, while each layer has its own material of a high or low refractive index value, and the total layers in a thickness of tens to hundreds nanometers are grown in this single structure. This invention is intended for optimizing the scanning of mechanism by modulating SPR resonant angle and wavelength, and for developing the prospect of portable instruments.

27 Claims, 5 Drawing Sheets

REPEATED STRUCTURE OF NANOMETER THIN FILMS WITH SYMMETRIC OR ASYMMETRIC CONFIGURATION FOR SPR SIGNAL MODULATION

FIELD OF THE INVENTION

The present invention relates generally to the research of a biomedical chip in sensing protein biomolecules by an optical method and more particularly relates to a procedure of coating a metal film on a surface plasmon resonance (SPR) device and a novel design of a multilayer structure.

BACKGROUND OF THE INVENTION

Disregard the fact that quite a few patents on genetic engineering related techniques have raised many legal and ethical issues, human beings have indeed made a big progress in knowing their own origin during the last century. A widely recognized discovery is the rough draft of the human genome, or the molecular sequence of DNA that comprises the human genes. A biochip, known as DNA microarrays, was designed in the late of last century for accelerating genetic research. This new technology is expected to detect the presence of a whole array of genetically based diseases, and, moreover, to conduct widespread disease screening.

A combination of molecular biology and microfabrication techniques has been applied to produce miniature analytical devices. This miniature analytical device is called a "biochip", and its device water is composed of glass, plastic, or silicon. The miniature analytical device also enables on-chip reactions and assays, which reduces volumes of reagents and raises density. Due to the variety of biochemical assays, reagents such as DNA probes, enzymes, antibodies or protein, are adhered to the surface of a biochip for various applications. Biochips are expected to revolutionize biology in the same way electronic chips revolutionized electronics.

Biochips will consistently grow smaller and more powerful with each new generation of biochip created. Additionally, the development of specialty biochips, made from various organic materials, can lead to new developments and utilizations. One encouraging development is the protein-based biochips. These biochips would be used to array protein substrates for drug lead screening, antibodies for diagnostic purposes, where the biochip then is also a biosensor, enzymes for catalytic reaction analysis and other applications. The basic construction of protein chips has some similarities to DNA chips, such as the use of a glass or plastic surface dotted with an array of molecules. These molecules can be DNA or antibodies that are designed to capture proteins. Protein microarrays are being used as powerful tools in high-throughput proteomics and drug discovery. Most of the current protein chips are based on the reactions between the capture proteins immobilized on a surface and the analyte proteins in the sample solution. A recent example of this technology shows, some Chinese scientists from laboratories announced they have invented a protein chip, which can rapidly diagnose severe acute respiratory syndrome (SARS). With the protein chip, doctors can tell SARS carriers from the suspects, as well as promptly monitor the latest development of the virus.

Although the DNA-chip marketplace is in its infancy, with considerable challenges remaining to be overcome, some techniques: DNA composition analysis, determination of a DNA sequence and quantitative analysis, capillary electrophoresis, nucleic acid amplification test, and gene expression analysis are progressing toward maturity. Furthermore, a series of other analytical methods, as a result of the mentioned techniques: cell separation, and cell-mediated immunity analysis are combined with combinatorial chemistry to feature a massive flux aspect while engaging the primitive screening for new medicine. The materials that are available presently for producing biochips include plastic film form technology, elastomer, and silicon. The focus of the biochips development in the field lately is on DNA applications which deserve an extra attention from us. A series of technology and product development are induced, subject to the requirements of DNA's sensing. For instance, prompt sensing and analytical techniques and products, DNA replication and splicing analysis techniques and products, and integrated DNA analytical systems.

Surface plasmon resonance (SPR) is a quantum optical-electrical phenomenon arising from the interaction of light with a metal surface. The energy carried by photons of light is transferred to packets of electrons, called plasmon, on a surface of metal under certain conditions.

Energy transfer occurs only at a specific resonance wavelength of light, which is an effect of equivalence in quantum energy of both the plasmon and photons. A surface plasmon sensor includes a dielectric block, a metal film which is formed on one face of the dielectric block and is brought into contact with the sample, a light source and an optical system which causes the light beam to enter the dielectric block and converges the light beam on the interface of the dielectric block and the metal film so that components of the light beam impinge upon the interface at various angles including angles of total reflection.

At certain wavelengths of incident light and angles, part of the incident light resonate across the metal and sample boundary, producing attenuation of the reflected signal—the surface plasmon resonance effect. This effectively corresponds to a change in refractive index at the surface. The magnitude of the effect depends upon the wavelength of the incident light, the angle of incidence, the mass density of the species adhered to the metal surface, and the refractive index and dielectric constant of the sample layer. The binding of the reagent and the analyte attached to the metal surface produces a change in the mass density on the metal surface, which as a result of the surface plasmon resonance effect, produces attenuation of the reflected signal.

Among the technologies on chip development, the optical methods for sensing are better choices for their sensitivity and resolution. Although fluorescence type gains many applications, surface plasmon resonance (SPR), as a research tool, has shown its advantages in quantifying pair of molecules interaction including: measurements are made in real-time and in situ, no labeling of either antibody or antigen molecules. Conventionally, biomolecular interactions are studied using techniques as immunoassays (ELISA or RIA), equilibrium dialysis, affinity chromatography and spectroscopy.

As a result, the SPR angle will change according to the amount of binding molecules. There is a linear relationship between the amount of binding molecules and the shift of the SPR angle. The SPR angle shifts in millidegrees as a response to quantify the binding of macromolecules to the sensor surface. A change of hundred millidegrees represents a change in surface protein coverage of approximately 1 $ng/mm^2$, or in bulk refractive index of approximately $10^{-3}$. The detection principle and penetration depth of the evanescent wave, 300–400 nm, limit the size of analyte to be measured. Macromolecules cannot be sensed in full size if it is wider than about 400 nm; consequently, the linear relationship is no longer valid. A qualitative analysis will, under these circumstances, take the place of the quantitative or kinetic analysis.

SUMMARY OF THE INVENTION

An object of the present invention is to achieve modulation of resonant angle and wavelength by utilizing the SPR principle through a symmetrical or asymmetrical multilayer structure in the Z-axis direction. The fabrication of this invention can have nanoscale thin film layers up to several hundreds, while each layer has its own material of a high or low refraction index value, and the total layers in a thickness of tens to hundreds nanometers are grown in this single structure.

Another object of the present invention is to apply this symmetrical or asymmetrical multilayer structure and an optical modulator to the design of SPR based chips and applications.

A further object of the invention is to apply this symmetrical or asymmetrical multilayer structure and an optical modulator to the design of disposable protein biosensing chips.

The present invention offers a novel construction of dielectric coupler, which substantially reduces the drawbacks of the existing devices, while tremendously improves the efficiency of the angular interrogation of mechanism and wavelength interrogation applications. With regard to the sensing of common SPR chips, the resonant angle after coated with a metal layer is usually about 74 deg in air, while 87 deg in liquid, which is difficult in calibration and measurement with scanning mechanism and inconvenient to use. The multilayer structure of this present invention enables a square-wave grating coupler based SPR system, through the adjustment of refractive index and thickness of the material, the resonance of wavelength and angular can be achieved.

BRIEF DESCRIPTION OF THE DRAWINGS

The invention can be more fully understood by reading the following detailed description of the preferred embodiments, with reference made to the accompanying drawings, wherein.

DETAILED DESCRIPTION OF THE INVENTION

Figure 1:
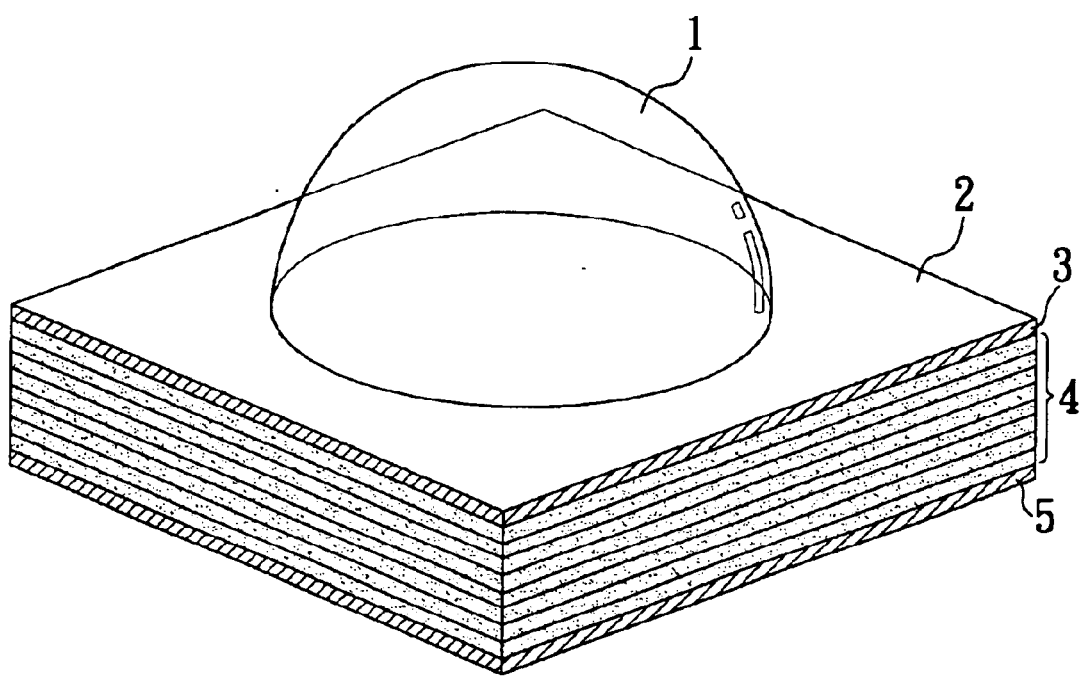
FIG. 1 is a schematic view of the present invention.
Figure 2:
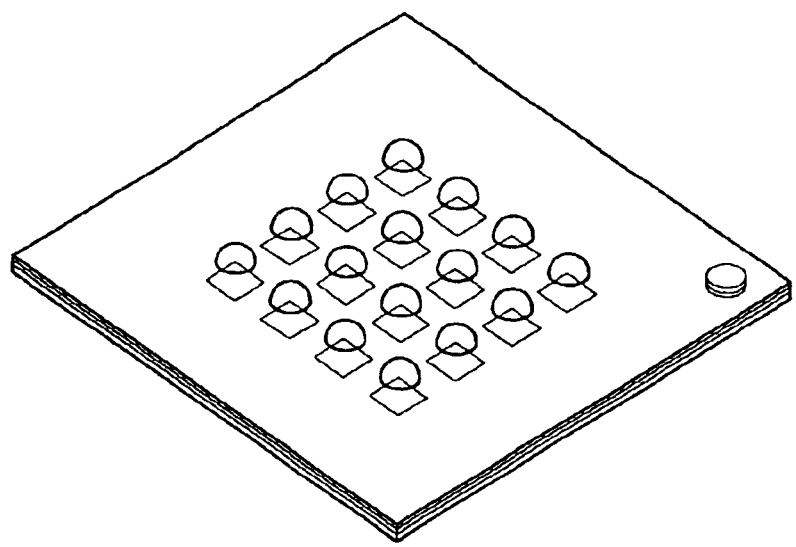
FIG. 2 is an illustrative front view of an array-based active SPR chip of the present invention.
Figure 3:
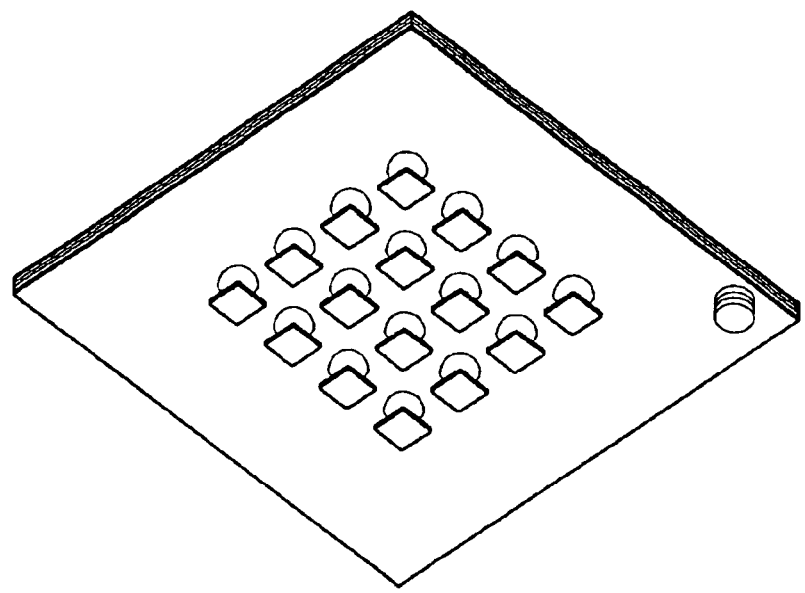
FIG. 3 is an illustrative bottom view of an array-based active SPR chip.

Embodiments of the present invention will now be described through a symmetric or asymmetric multilayer structure in an active surface plasmon resonance (SPR) chip, with reference to the accompanying figures. Referring first to FIG. 1, a symmetric or asymmetric multilayer structure in an active surface plasmon resonance (SPR) chip comprising: a prism 1, a substrate material 2, a thin gold film (can be other metal film) 3, a nanometer multilayer dielectric thin films 4, and a thin gold film 5.

The interposed stack of nanometer multilayer thin films is organized by the materials of a high and low refractive index alternately, and the thickness of each layer is set a fraction of wavelength of the incident light, which is about a tens to several hundreds of nanometers. Number of total layers is dependent on the equivalent refractive index as that in a single dielectric layer.

Material of a high or low refractive index can be viewed as a constituent of a "pair", and a few pairs to tens of pairs in general are the whole. A modulated resonance of angle and wavelength is subject to the equivalence of desired refractive index formed by the multiple layers, while the thickness of the total layers is no less than about nine hundred nanometers. Materials of high and low refractive indices are made of following compounds: ZnS, MgF, GaN, ITO, ZnTe, BeZnTe, MgSe/BeZnTe, InGaAs, InP, GaAs, $Al_xGa_{1-x}As$, GaAsSb, $Al_xGa_{1-x}N$ and the like. Desired materials also include the coupling of metal (gold, silver) and dielectric layer. A biochip can be fabricated by a nanometer multilayer thin films structure thereto coupling to glass or crystal substrate, and is coated with binding biomolecules or other reagents on the metal surface.

For purpose of illustration, the interposed nanometer thin films of the present invention, like the multilayer dielectric stack of the prior art, is shown in FIG. 1 as comprised of eight layers. Actually, the first preferable embodiment as the result shown in FIGS. 4 and 5 has six interposed layers, Prism/L/H/L/H/L/H/Au/Sample, of dielectric thin films in the overall chip structure for water sample, while the second preferable embodiment as shown in FIG. 6 through 9 has eight layers of dielectric thin films as a modification from the first embodiment, Prism/L/H/L/H/L/H/Au/Sample, in the overall chip structure for water and alcohol sample.

Figure 4:
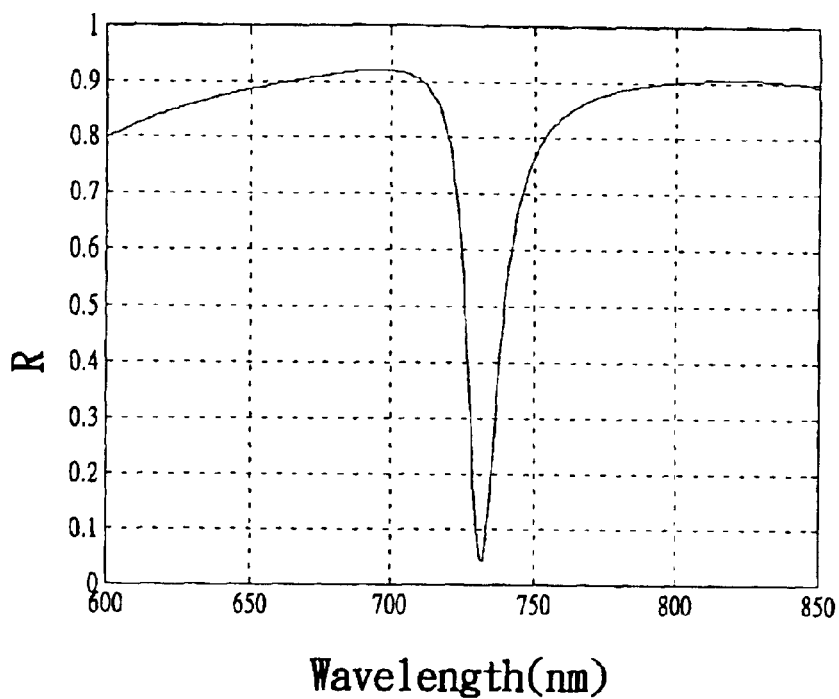
FIG. 4 shows resonant wavelength with regard to reflective ratio in modulated angle with water sample.
Figure 5:
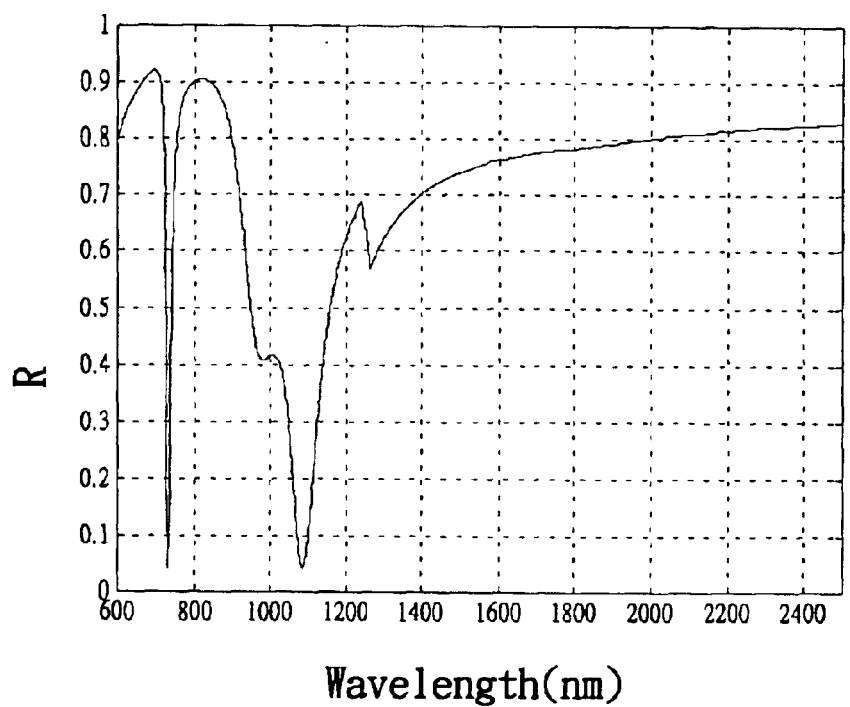
FIG. 5 shows resonant wavelength with regard to reflective ratio in modulated wavelength with water sample.

The observed resonant wavelengths with regard to a set of reflective ratios obtained by way of angular and wavelength interrogations respectively are shown in the FIGS. 4 and 5, the resonant conditions of these two experiments are further recognized as the consequence of the attenuate total reflection (ATR) principle. Within the first preferred embodiment, the setup for the two experiments includes 65 degrees as the incident angle of light and 1.33 as the refractive index of water.

The analytical sample within the second preferred embodiment utilizes water and alcohol, which is used for the following four experiments under the same configuration as that in the first preferred embodiment, and the experimental results will be shown in FIG. 6 through 9.

Figure 6:
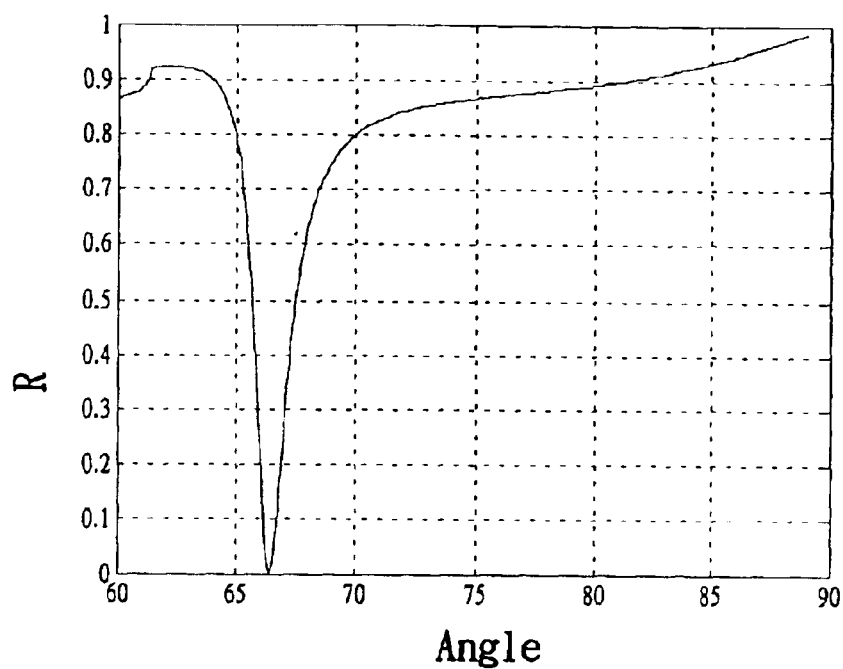
FIG. 6 shows resonant angle with regard to reflective ratio in modulated angle with water and alcohol sample.
Figure 7:
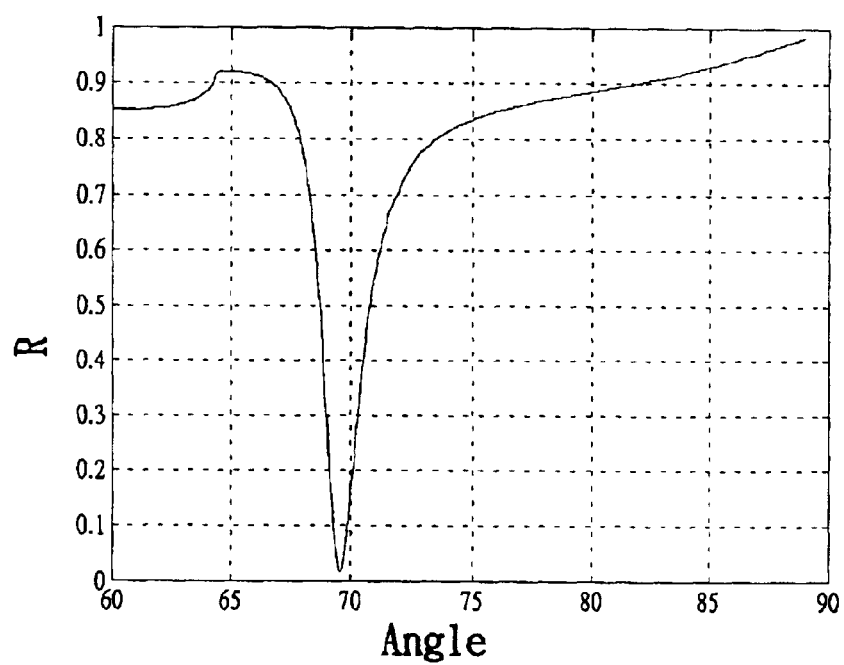
FIG. 7 shows resonant angle with regard to reflective ratio in modulated wavelength with water and alcohol sample.
Figure 8:
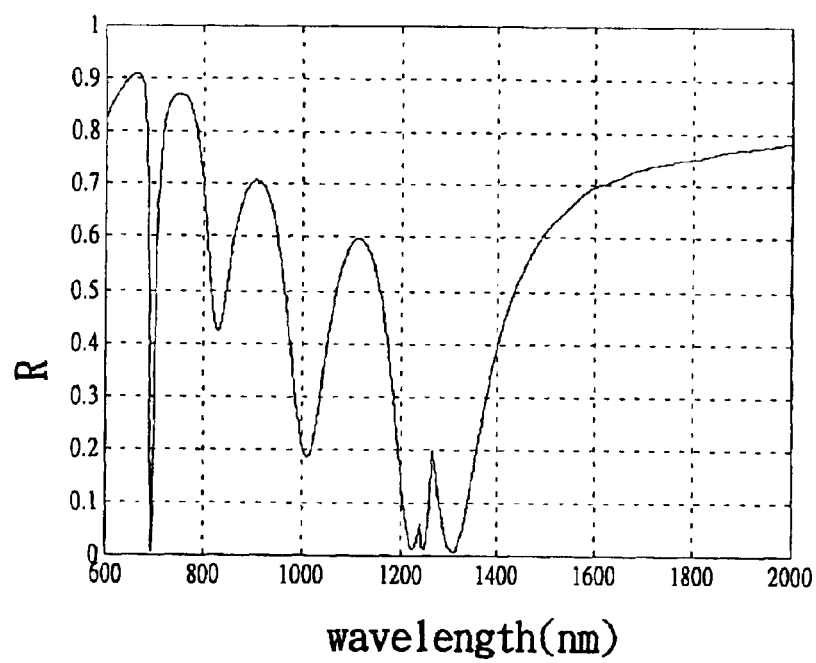
FIG. 8 shows resonant wavelength with regard to reflective ratio in modulated angle with water and alcohol sample.
Figure 9:
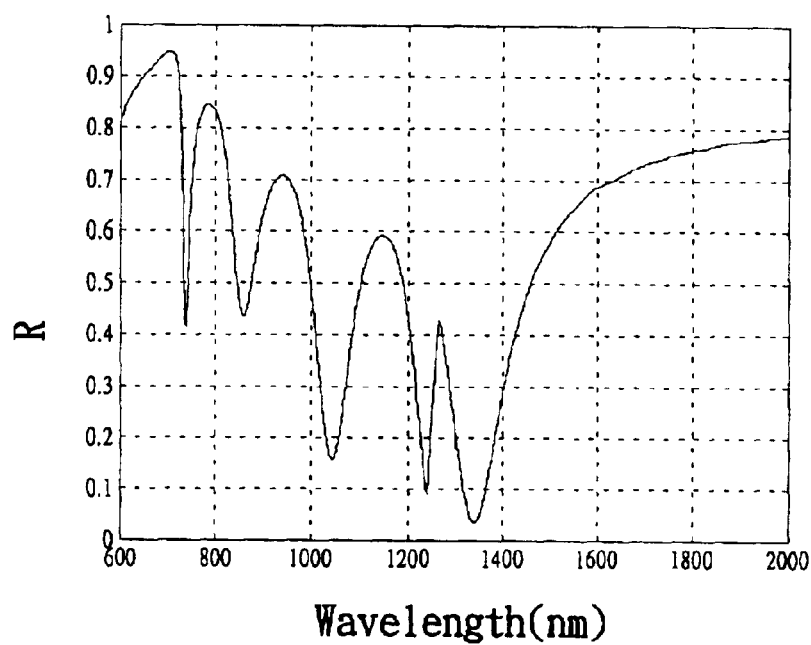
FIG. 9 shows resonant wavelength with regard to reflective ratio in modulated wavelength with water and alcohol sample.

Experiments shown by FIGS. 6 and 7 are focused on the resonant angles with regard to a set of reflective ratios obtained by angular and wavelength interrogations respectively, and the setup for the two experiments includes a 632.8 nm as wavelength of incident light and 1.33 and 1.3652 as the refractive indices of water and alcohol respectively. Resonant wavelengths are the desired object in FIGS. 8 and 9, the setup for the two experiments includes 65 degrees as the incident angle of light and 1.33 and 1.3652 as the refractive indices of water and alcohol respectively.

According to the comparison between the preferred embodiments thereto and the traditional metal coated SPR chip, the embodiments based on angular modulation technique substantially raise the performance such as: resonant angle changes up to 10 deg. (from 70 down to 60), resonant amplitude alters about 20 times, and as a consequence, the signal to noise ratio improves 180 times. Furthermore, the embodiments based on wavelength modulation technique substantially raise the performance such as: resonant wavelength changes up to 130 nm (from NIR down to VIS), FWHM alters about 3 times, and as a consequence, capable to offer narrower bandwidth of spectrum for visual sensing applications, and support multi-wavelength modules in engaging multi-channel efficiency verification.

What is claimed is:

1. An active surface plasmon resonance (SPR) chip, comprising:
   a first layer of metal;
   an outmost layer of metal; and
   a nanometer multilayer structure having a high refractive index of material and a low refractive index of material to form at least a monolayer structure interposed between said first layer of material and said outmost layer of material such that resonant angle and wavelength occurs through an arrangement of said nanometer multilayer structure.

2. An active SPR chip as recited in claim 1, wherein said first layer of material and said outmost layer of metal can be a same material, thereby presenting a symmetry structure.

3. An active SPR chip as recited in claim 1, wherein said first layer of material and said outmost layer of metal can be a different material, thereby presenting an asymmetry structure.

4. An active SPR chip as recited in claim 1, wherein said active SPR chip adopts Sputter as a first method for developing thin film deposition.

5. An active SPR chip as recited in claim 1, wherein said active SPR chip adopts CVD as a second method for developing said thin film deposition.

6. An active SPR chip as recited in claim 1, wherein said active SPR chip adopts MBE as a third method for developing said thin film deposition.

7. An active SPR chip as recited in claim 1, wherein said active SPR chip adopts a partial method of VCSEL for developing.

8. An active SPR chip as recited in claim 1, wherein said active SPR chip adopts MicroElectroMechanical process technique as a method for fabrication.

9. An active SPR chip as recited in claim 1, wherein each layer in a plurality of layers of said nanometer multilayer structure has a thickness of 10 up to 1,000 nanometers.

10. An active SPR chip as recited in claim 1, wherein said nanometer multilayer structure is composed of a plurality of pairs of materials, said pair being formed by said high refractive index of material and said low refractive index of material, and number of said pairs can be from 1 up to tens.

11. An active SPR chip as recited in claim 1, wherein a total of a plurality of said layers in said nanometer multilayer structure has a thickness no more than 900 nanometers.

12. An active SPR chip as recited in claim 1, wherein said high refractive index of material and said low refractive index of material is Zinc Sulfide.

13. An active SPR chip as recited in claim 1, wherein said high refractive index of material and said low refractive index of material is Magnesium Fluoride.

14. An active SPR chip as recited in claim 1, wherein said high refractive index of material and said low refractive index of material is GaN.

15. An active SPR chip as recited in claim 1, wherein said high refractive index of material and said low refractive index of material is ITO.

16. An active SPR chip as recited in claim 1, wherein said high refractive index of material and said low refractive index of material is ZnTe.

17. An active SPR chip as recited in claim 1, wherein said high refractive index of material and said low refractive index of material is BeZnTe.

18. An active SPR chip as recited in claim 1, wherein said high refractive index of material and said low refractive index of material is MgSe/BeZnTe.

19. An active SPR chip as recited in claim 1, wherein said high refractive index of material and said low refractive index of material is InGaAs.

20. An active SPR chip as recited in claim 1, wherein said high refractive index of material and said low refractive index of material is InP.

21. An active SPR chip as recited in claim 1, wherein said high refractive index of material and said low refractive index of material is GaAs.

22. An active SPR chip as recited in claim 1, wherein said high refractive index of material and said low refractive index of material is $Al_xGa_{1-x}As$.

23. An active SPR chip as recited in claim 1, wherein said high refractive index of material and said low refractive index of material is GaAsSb.

24. An active SPR chip as recited in claim 1, wherein said high refractive index of material and said low refractive index of material is $Al_xGa_{1-x}N$.

25. An active SPR chip as recited in claim 1, wherein said high refractive index of material and said low refractive index of material forms different metallic-dielectric boundary.

26. An active SPR chip as recited in claim 1, wherein said first layer of material couples to crystal or glass substrate.

27. An active SPR chip as recited in claim 1, wherein said first layer of material is coated with binding biomolecules.

* * * * *